United States Patent [19]

Knobloch et al.

[11] 3,948,982

[45] Apr. 6, 1976

[54] POLYHALOBENZENEPOLYCARBOXYLIC ACID PROCESSES

[75] Inventors: James O. Knobloch, Naperville; James P. Nelson, Woodridge; John B. L. Harkness, Naperville, all of Ill.

[73] Assignee: Standard Oil Company, Chicago, Ill.

[22] Filed: Sept. 10, 1973

[21] Appl. No.: 395,719

[52] U.S. Cl. .............................................. 260/525
[51] Int. Cl.² ...................................... C07C 51/42
[58] Field of Search ............ 260/525, 524 S, 515 A

[56] References Cited
UNITED STATES PATENTS
3,142,701  7/1964  Wilkinson...................... 260/515 A Primary Examiner—Anton H. Sutto
Attorney, Agent, or Firm—William H. Magidson; Arthur G. Gilkes; William T. McClain

[57] ABSTRACT

Isolation of polyhalobenzenepolycarboxylic acids from a sulfuric acid medium by diluting said sulfuric acid medium with liquid sulfur dioxide and partitioning said polyhalobenzenepolycarboxylic acids from said sulfuric acid medium.

12 Claims, No Drawings

POLYHALOBENZENEPOLYCARBOXYLIC ACID PROCESSES

This invention relates to a method of isolating polyhalobenzenepolycarboxylic acids from a sulfuric acid medium. More particularly this invention relates to a method of isolating 2,5-dibromoterephthalic acid from a sulfuric acid medium.

Recently, there has been considerable interest in the production of fire retardant fibers, particularly those where the fire retardancy is built into the polymer chain of the fiber. In the case of polyesters (e.g. polyethylene terephthalate), various halogenated dicarboxylic acids have been suggested. Of these 2,5-dibromoterephthalic acid appears to be best because of its high rate of reactivity in polyesterification reactions and the relatively high concentration of halogen that can be incorporated into the fiber per diacyl moiety. 2,5-dichloroterephthalic acid is unsuitable since it is difficult to incorporate enough halogen into the polymer to obtain the desired fire retardancy. The various other bromo and chloro substituted terephthalic acids are unsuitable for this use because of steric hindrance in condensation polyesterification reactions (the various tri and tetrahaloterephthalic acids), low halogen content and/or difficulty in producing the desired acid.

U.S. Pat. No. 3,142,701 which is hereby incorporated by reference, discloses a method of producing 2,5-dibromoterephthalic acid by reacting substantially equal molar quantities of bromine and terephthalic acid in an oleum solution (fuming sulfuric acid). For each mole of bromine consumed in this reaction two moles of sulfur trioxide are converted to one mole of sulfur dioxide and one mole of sulfuric acid. Although the 2,5-dibromoterephthalic acid is insoluble in the oleum reaction medium, it is extremely difficult to separate from the reaction by-products (terephthalic acid, tribromoterephthalic acid, tetrabromoterephthalic acid, etc.) due to the high viscosity of the reaction medium and the solubility properties of the various acids. Separation of solids by partitioning (filtration and/or centrifugation) is very slow due to the high viscosity of the reaction product suspension. Further, the partitioned reaction product contains a considerable quantity of occluded oleum, which in turn contains substantial quantities of the aforesaid by-product organic acids. Attempts to remove the occluded solvent by washing with water is unsatisfactory since the by-product organic acids precipitate thereby contaminating the 2,5-dibromoterephthalic acid. When 2,5-dibromoterephthalic acid is contaminated with substantial amounts of tri and tetrabromoterephthalic acid by-products, the 2,5-dibromoterephthalic acid is unsuitable for the production of fiber forming polyesters due to the lower degree of polymerization of the polyester which is due to the low reactivity of these by-product acids. Attempts to remove the occluded solvent by washing with fresh sulfuric acid results in substantially lower yields of 2,5-dibromoterephthalic acid since this organic acid is fairly soluble in sulfuric acid. Accordingly, there is a need for more efficient methods of recovering substantially pure 2,5-dibromoterephthalic acid from sulfuric acid mediums.

The general object of the invention is to provide a new method of isolating polyhalobenzenepolycarboxylic acids from a sulfuric acid medium.

The principal object of this invention is to provide an improved method of separating 2,5-dibromoterephthalic acid from oleum.

A further object of this invention is to provide an improved method of recovering 2,5-dibromoterephthalic acid containing low levels of tri and tetrabromoterephthalic acid from sulfuric acid mediums.

Other objects appear hereinafter.

For the purpose of this invention, "sulfuric acid" is used in a generic sense to include oleum.

The objects of this invention can be attained by using sulfur dioxide as a diluent and/or antisolvent for polyhalobenzenepolycarboxylic acid sulfuric acid systems. Although liquid sulfur dioxide is an extremely poor solvent for benzenepolycarboxylic acids and halo substituted benzenepolycarboxylic acids, liquid sulfur dioxide can be added, in a suitable concentration, to oleum without altering the solvating properties of the oleum while lowering the viscosity of the oleum system (suspension, in the case of 2,5-dibromoterephthalic acid produced in oleum by the method of U.S. Pat. No. 3,142,701) so that partitioning can be carried out at a rapid rate. After the initial partitioning, occluded oleum can be removed easily by washing with liquid sulfur dioxide. Since sulfur dioxide is a by-product of the aforesaid bromination of terephthalic acid, its use as a diluent or wash has the additional advantage that its use does not introduce an additional impurity.

In those cases where it is desirable to recover other polyhalobenzenepolycarboxylic acids, such as tetrabromoterephthalic acid, tetrachloroterephthalic, etc. from sulfuric acid or oleum solutions, liquid sulfur dioxide can be added in sufficiently high concentrations to precipitate dissolved polyhalobenzenepolycarboxylic acids from the sulfuric acid medium. The liquid sulfur dioxide (boiling point −10°C) has the additional advantage that it can be recovered readily from the sulfuric acid medium thereby minimizing recovery costs of both sulfur dioxide and sulfuric acid.

While this invention is generally useful in the isolation of polyhalobenzenepolycarboxylic acids from sulfuric acid mediums, it is particularly useful for the isolation of pure 2,5-dibromoterephthalic acid from oleum. Accordingly, the description following is made with reference to the isolation of this acid.

In somewhat greater detail, 2,5-dibromoterephthalic acid is produced by reacting substantially equal molar quantities of bromine and terephthalic acid (0.5 to 1.5 moles bromine per mole terephthalic acid) in oleum (containing at least 25 percent by weight sulfur trioxide, preferably at least 40 percent by weight sulfur trioxide,) using an iodine catalyst. Typically terephthalic acid and bromine constitute about 15 to 35 percent by weight of the reaction medium (catalyst and oleum constitute 85 to 65 percent by weight). After the bromination reaction is complete, the various organic acids present in the oleum reaction product constitute about 10 to 33 percent by weight of the sulfuric acid medium.

The viscous sulfuric acid (oleum) suspension is diluted with about 50 to 350 parts by weight (preferably 75 to 200 parts by weight) liquid sulfur dioxide per 100 parts by weight sulfuric acid (oleum) suspension. The higher the concentration of sulfur dioxide, the lower the viscosity of the suspension and the greater the tendency for the dissolved organic acids (terephthalic acid, tribromoterephthalic acid and tetrabromoterephthalic acid) to be precipitated from the solvent. Within the preferred range of 75 to 200 parts by weight liquid sulfur dioxide per 100 parts by weight sulfuric acid suspension, the suspension can be partitioned rapidly without precipitating unduly high concentrations of dissolved organic acids. The sulfur dioxide diluted suspension can be partitioned rapidly by any suitable means, such as by filtration or centrifugation.

As indicated above, the sulfur dioxide is maintained in the liquid. This can be accomplished by maintaining the suspension below the boiling point of sulfur dioxide or by partitioning under pressure.

The partitioned 2,5-dibromoterephthalic acids solids which generally contain a substantial concentration of occluded oleum solvent can then be freed from the oleum by washing with additional liquid sulfur dioxide. Alternatively, the 2,5-dibromoterephthalic acid solids can be reslurried in liquid sulfur dioxide and partitioned again to remove most of the occluded oleum. Any occluded sulfur dioxide can be recovered by heating to drive off this low boiling (b.p. −10°C) liquid. Since the 2,5-dibromoterephthalic acid solids generally contain some sulfur trioxide, this valuable material can be recovered by heating the solids in a dryer.

Although this invention is primarily directed to improved methods of isolating 2,5-dibromoterephthalic acid from sulfuric acid mediums, essentially the same liquid sulfur dioxide dilution and washing techniques can be used to reduce the viscosity of other polyhalobenzenepolycarboxylic acid/sulfuric acid system. Further, when in excess of about 250 parts by weight liquid sulfur dioxide is mixed per 100 parts by weight oleum, various dissolved polyhalobenzenepolycarboxylic acids, (tetrabromo, tribromo, tetrachloro and trichloroterephthalic acid, trichloro or tribromo trimellitic acid) can be precipitated from the sulfuric acid medium thereby facilitating recovery.

EXAMPLE I

Six hundred two and six-tenths grams of a crude 2,5-dibromoterephthalic acid/oleum suspension (containing about 21% by weight aromatic dicarboxylic acids) was placed in a 4-neck flask equipped with an addition funnel, stirrer and a cold finger condenser (dry ice-isopropanol cooled). After the flask was cooled to −6°C, 450 ml liquid (640g) sulfur dioxide (approximately 106 grams sulfur dioxide per 100 grams oleum suspension) was added over a 67 minute period with stirring. The diluted suspension was centrifuged at −10°C using an International Chemical Centrifuge having a 5 inches diameter perforated bowl and a glass cloth at 3,000 r.p.m. The drain rate was more than 10 lb/min/sq ft. and yielded a ¼ inch thick cake.

After washing with two 375 ml portions of liquid sulfur dioxide, the 200.4 gram cake was dried in a 50°C vacuum oven for 16 hours yielding 135.2 grams of impure product. One hundred twenty-four and eight-tenths grams of this cake lost 2.8 grams on vacuum drying for 4½ hours at 78°C. Forty-five and three-tenths grams of the twice vacuum dried product was dispersed in 200 grams water, heated on a steam cone for 1 hour, cooled, filtered, washed with 25 ml water and dried to yield 29.8 grams dry weight.

The crude 2,5-dibromoterephthalic acid/oleum suspension used in this example was produced by reacting terephthalic acid with bromine in oleum (50.0 wt. %SO$_3$) using 0.682%I$_2$ based on the weight of the terephthalic acid at 47°–55°C for 3-3/4 hours. The weight ratio of oleum to terephthalic acid was 5.99 to 1 and 0.715 moles of bromine was used per mole of terephthalic acid.

EXAMPLE II

This example illustrates the poor rate of filtration when liquid sulfur dioxide is not used as a diluent. Nine hundred thirty and three-tenths grams of a crude 2,5-dibromoterephthalic acid/oleum suspension (containing about 22% by weight aromatic dicarboxylic acids) was centrifuged at 25°C using the same International Chemical Centrifuge used in Example I. The drain rate was 0.5 to 1.0 lbs/min/sq ft at 3,000 r.p.m. The cake was about ½ inch and weighed 408.8 grams.

Accordingly, the sulfur dioxide dilution technique in Example I enables one to separate the aromatic dicarboxylic acids at a rate 10 times faster than if the sulfur dioxide dilution was omitted. Further, the combined sulfur dioxide dilution and sulfur dioxide wash results in a centrifuge cake approximately half the weight and volume of the centrifuge cake produced in this example in spite of the fact that only about 10% by weight more organic acids were present in the 930.3 grams of starting oleum suspension used in this example.

Thirty-two and six-tenths grams of the centrifuge cake was dispersed in 151.1 grams water, heated on a steam cone for 1 hour, cooled, filtered, washed with 20 ml water and dried to yield 12.3 grams dry weight product.

EXAMPLE III

Samples of the water washed centrifuge cakes of Examples I and II were esterified with diazomethane and analyzed by gas chromatography. The results are set forth below in Table I:

TABLE I

| Organic Acid | Example I Wt.% | Example II Wt.% |
|---|---|---|
| Terephthalic Acid | .856 | 6.10 |
| Bromoterephthalic Acid | 11.5 | 11.7 |
| Iodoterephthalic Acid | .029 | .110 |
| 2,5-dibromoterephthalic acid | 86.9 | 73.6 |
| 2,3-dibromoterephthalic acid | .406 | 1.19 |
| Tribromoterephthalic acid | .482 | 1.79 |
| Tetrabromoterephthalic acid | .005 | 0 |

The above data clearly illustrates that sulfur dioxide dilution and washing technique of this invention result in markedly higher yields of the desired 2,5-dibromoterephthalic acid and much lower levels of terephthalic acid and tribromoterephthalic acid impurities.

EXAMPLE IV

This example illustrates the use of more than the optimum concentration of liquid sulfur dioxide as a diluent. Five hundred sixty-five and eight-tenths grams of a crude 2,5-dibromoterephthalic acid/oleum suspension (containing about 20% by weight aromatic dicarboxylic acids) was diluted with 1,780 grams sulfur dioxide (314 grams sulfur dioxide per 100 grams oleum suspension) in the manner described in Example I and centrifuged under the same conditions. The drain rate was more than 10 lbs/min/sq ft and yielded a ¼ inch cake.

After washing with 750 ml of liquid sulfur dioxide, the 177.9 gram cake was maintained at 50°C in a vacuum oven for 64 hours yielding 139.6 grams of product. Residual inorganic acid (sulfur trioxide and sulfuric acid) were removed by slurrying 30.2 grams of product in 137.4 grams water, digesting, cooling and drying in the manner set forth in Example I, yielding 19.0 g. This product was esterified with diazomethane and gas chromatography indicated that the product was 81% by weight 2,5-dibromoterephthalic acid, 11.8% by weight monobromoterephthalic, 5.06% by weight terephthalic acid, 0.952% by weight 2,3-dibromoterephthalic acid, 0.932% by weight tribromoterephthalic acid and 0.043% by weight iodoterephthalic acid.

Accordingly, the use of excess sulfur dioxide diluent enhances partitioning and results in a product of higher purity than can be obtained without sulfur dioxide dilution and washing.

EXAMPLE V

When Example IV is repeated using 50 parts by weight sulfur dioxide diluent per 100 parts by weight 2,5-dibromoterephthalic acid/oleum suspension, the centrifuge rate is 1 lb/min/sq ft and ⅜ inch cake is obtained. This rate is somewhat faster than the rate of Example II.

The sulfur dioxide washed product, reslurried in water and dried had 84.4% by weight 2,5-dibromoterephthalic acid, 0.716% by weight terephthalic contamination and 2.21% by weight tetrabromoterephthalic acid contamination.

We claim:

1. The process of isolating a polyhalobenzenepolycarboxylic acid from a sulfuric acid medium comprising diluting said sulfuric acid medium with liquid sulfur dioxide and partitioning said polyhalobenzenepolycarboxylic acid from said sulfuric acid medium.

2. The process of claim 1, wherein said sulfuric acid medium contains from about 10 to 33 percent by weight organic acids.

3. The process of claim 1, wherein said sulfuric acid medium is diluted with at least 50 parts by weight liquid sulfur dioxide per each 100 parts by weight sulfuric acid medium.

4. The process of claim 1, wherein the partitioned polyhalobenzenepolycarboxylic acid is washed with liquid sulfur dioxide to remove occluded sulfuric acid.

5. The process of claim 1, wherein the partitioned polyhalobenzenepolycarboxylic acid is reslurried in liquid sulfur dioxide and partitioned again to remove occluded sulfuric acid.

6. The process of isolating 2,5-dibromoterephthalic acid from a sulfuric acid suspension comprising diluting said sulfuric acid suspension with liquid sulfur dioxide and partitioning said 2,5-dibromoterephthalic acid from said sulfuric acid medium.

7. The process of claim 6, wherein said sulfuric acid suspension contains from about 10 to 33 percent by weight organic acids.

8. The process of claim 6, wherein said sulfuric acid suspension is diluted with at least 50 parts by weight liquid sulfur dioxide per each 100 parts by weight sulfuric acid suspension.

9. The process of claim 6, wherein the partitioned 2,5-dibromoterephthalic acid is washed with liquid sulfur dioxide to remove occluded sulfuric acid.

10. The process of claim 6, wherein the partitioned 2,5-dibromoterephthalic acid is reslurried in liquid sulfur dioxide and partitioned again to remove occluded sulfuric acid.

11. The process of claim 9, wherein occluded sulfur trioxide is recovered by heating.

12. The process of claim 10, wherein occluded sulfur trioxide is recovered by heating.

* * * * *